United States Patent [19]

Bogdansky et al.

[11] Patent Number: 5,284,655
[45] Date of Patent: Feb. 8, 1994

[54] SWOLLEN DEMINERALIZED BONE PARTICLES, FLOWABLE OSTEOGENIC COMPOSITION CONTAINING SAME AND USE OF THE COMPOSITION IN THE REPAIR OF OSSEOUS DEFECTS

[75] Inventors: Simon Bogdansky, Marlboro; Robert K. O'Leary, Spring Lake, both of N.J.

[73] Assignee: Osteotech, Inc., Shrewsbury, N.J.

[21] Appl. No.: 830,942

[22] Filed: Feb. 4, 1992

Related U.S. Application Data

[63] Continuation-in-part of Ser. No. 573,458, Aug. 27, 1990, which is a continuation-in-part of Ser. No. 410,596, Sep. 21, 1989, Pat. No. 5,073,373.

[51] Int. Cl.$^5$ .................. A61K 35/32; A61K 47/26; A61K 47/36
[52] U.S. Cl. .................................. 424/422; 424/423; 424/549; 514/777; 514/779; 514/780; 514/782; 623/16
[58] Field of Search ............... 424/422, 423, 549; 623/16

[56] References Cited

U.S. PATENT DOCUMENTS

| | | | |
|---|---|---|---|
| 3,458,397 | 6/1969 | Myers et al. | 424/549 |
| 4,191,747 | 3/1980 | Scheicher | 424/94 |
| 4,440,750 | 4/1984 | Glowacki et al. | 424/95 |
| 4,458,733 | 7/1984 | Lyons | 141/1 |
| 4,563,489 | 1/1986 | Urist | 514/21 |
| 4,595,713 | 6/1986 | St. John | 424/423 |
| 5,053,049 | 10/1991 | Campbell | 623/16 |
| 5,162,114 | 11/1992 | Kuberasampath et al. | 424/423 |

FOREIGN PATENT DOCUMENTS 0880425  11/1981  U.S.S.R. ................... 424/549

OTHER PUBLICATIONS

"Induced Osteogenesis for Repair and Construction in the Craniofacial Region" Mulliken, J. B. and Glowacki, J. Plastic and Reconstructive Surgery, May 1980, pp. 553–559.

*Primary Examiner*—Thurman K. Page
*Assistant Examiner*—James M. Spear
*Attorney, Agent, or Firm*—Dilworth & Barrese

[57] ABSTRACT

Swollen demineralized bone particles are formulated into a flowable osteogenic composition which is useful in the repair of osseous defects.

18 Claims, No Drawings

SWOLLEN DEMINERALIZED BONE PARTICLES, FLOWABLE OSTEOGENIC COMPOSITION CONTAINING SAME AND USE OF THE COMPOSITION IN THE REPAIR OF OSSEOUS DEFECTS

CROSS REFERENCE TO RELATED APPLICATIONS

This application is a continuation-in-part of commonly assigned copending U.S. patent application Ser. No. 07/573,458, filed Aug. 27, 1990 as a continuation-in-part of commonly assigned copending U.S. patent application Ser. No. 07/410,596, filed Sept. 21, 1989 and issued Dec. 17, 1991 as U.S. Pat. No. 5,073,373.

BACKGROUND OF THE INVENTION

This invention relates to a demineralized bone product and in particular, to an osteogenic composition containing swollen particles of demineralized bone substantially uniformly distributed within a biocompatible fluid carrier and to the use of the composition in the repair of osseous defects.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *Orthopaedic Review*, Vol. XVII, No. 8, pp. 857-863 (August, 1989).

According to Habal et al., "Autologous Corticocancellous Bone Paste for Long Bone Discontinuity Defects: An Experimental Approach", *Annals of Plastic Surgery*, Vol. 15, No. 2, pp. 138-142 (Aug. 1985), autogenous bone which has been granulated into a pastelike material and combined with autogenous blood has been used in the repair of long bone defects in dogs.

SUMMARY OF THE INVENTION

It is a principal object of the invention to provide swollen particles of demineralized cortical cancellous and/or corticoncancellous autogenous, allogenic or xenogenic bone tissue.

It is a specific object of the invention to provide a flowable osteogenic composition comprising swollen demineralized bone particles substantially uniformly distributed within a biocompatible fluid carrier therefor and to apply the composition to a bone defect site to induce new bone ingrowth at the site.

It is another specific object of the invention to provide a flowable osteogenic composition containing swollen particles of demineralized bone within a biocompatible fluid carrier which is a polyhydroxy compound such as glycerol.

It is yet another specific object of the invention to provide a flowable osteogenic composition of putty-like consistency containing swollen particles of demineralized bone and as carrier therefor an aqueous solution of a polysaccharide such as dextran.

In keeping with these and related objects of the invention, there are provided swollen particles of demineralized bone and a flowable osteogenic composition comprising such particles substantially uniformly distributed within a biocompatible fluid carrier.

Application of the foregoing osteogenic composition to the site of an osseous defect, e.g., one resulting from injury, infection, malignancy or developmental malformation, leads to rapid new bone ingrowth by one or more mechanisms such as osteogenesis, osteoconduction and osteoinduction.

The osteogenic composition of this invention can be readily prepared as needed, preferably with the components of the composition, the means for their combination to provide the composition and the means for applying the composition to a bone defect site being provided in the form of a unitary kit or package. Alternatively, the osteogenic composition can be prepared in advance and stored in the sterile condition for later use, optionally within the means which will be used to apply the composition to a bone defect site.

DESCRIPTION OF THE PREFERRED EMBODIMENTS

The term "flowable" as applied to the osteogenic composition of this invention shall be understood to refer to the ability of the composition to flow either of its own accord or under the influence of some mechanical force. Thus, osteogenic compositions of paste- or putty-like consistency as well as those of liquid or runny consistency are properly referred to as "flowable" within the context of the present invention.

The demineralized bone particles of the osteogenic composition herein are a known type of material and can be obtained in accordance with known procedures. The expression "bone particles" shall be understood to refer to a quantity of individual particles the major proportion of which, e.g., at least about 60 percent by weight and preferably at least about 70 percent by weight, possess, prior to swelling, a maximum dimension of not greater than about 10 mm, preferably not greater than about 5 Mm and most preferably not greater than about 1 mm. Thus, e.g., the demineralized bone particles employed in the osteogenic composition of this invention can range in size from relatively coarse particles or chips whose maximum dimension is from about 1 to about 10 mm to relatively fine particles or powders whose maximum dimension is from about 0.01 to about 0.5 mm (from about 10 to about 500 microns).

The bone particles can be obtained from cortical, cancellous and/or corticocancellous autogenous, allogeneic or xenogeneic bone tissue.

In a preferred bone demineralization procedure, the bone is first pulverized to the desired average particle size followed by defatting/disinfecting and acid demineralization treatments. A preferred defatting/disinfectant solution is an aqueous solution of ethanol, the ethanol being a good solvent for lipids and the water being a good hydrophilic carrier to enable the solution to penetrate more deeply into the bone. The aqueous ethanol solution also disinfects the bone by killing vegetative microorganisms and viruses. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably 70% alcohol. Following defatting, the bone is immersed in acid over time to effect demineralization. Acids which can be employed in this operation include inorganic acids such as hydrochloric acid and organic acids such as peracetic acid. After acid treatment, the demineralized bone particles are rinsed with sterile water for injection, buffered with a buffering agent to a final predetermined pH and then finally rinsed with water for injection to remove residual amounts of acid and buffering agent. The demineralized bone particles can be used immediately for preparation of the swollen particles of this invention or they can be stored under aseptic conditions, advantageously in a freeze-dried state, prior to such preparation.

If desired, the demineralized bone particles can be modified in one or more ways, e.g., the porosity of the bone particles can be increased and/or the bone particles can be treated with one or more modifying agents, e.g. glutaraldehyde, as disclosed in U.S. Pat. No. 4,678,470. Another optional treatment involves augmenting or altering the bone protein content of the bone particles as described in U.S. Pat. Nos. 4,743,259 and 4,902,296.

Swelling of the demineralized bone particles can be accomplished merely by contacting the particles with a sufficient quantity of liquid swelling agent for a period of time sufficient to result in some appreciable degree of swelling. Swelling will be observed as an increase in the volume and weight of the bone particles due to their taking up some amount of swelling agent. In addition, as the particles swell, they become somewhat transparent, such being yet another characteristic of the swollen demineralized bone particles herein.

As a generality, the smaller the particles (and therefore the greater their surface area per volume), the greater will be the degree of swelling, all other conditions remaining the same. As the period of contact between the bone particles and liquid swelling agent increases, the degree of swelling of the particles will increase until some maximum, or equilibrium, level of swelling is achieved. The bone particles can be utilized herein even though they have not reached the maximum degree of swelling provided, of course, at least an appreciable amount of swelling has occurred. In general, an average increase in volume and/or weight of the swollen particles relative to the volume and/or weight of the unswollen particles on the order of at least about 10 percent, preferably at least about 20 percent and more preferably at least about 30 percent is entirely satisfactory.

Among the suitable swelling agents which can be used herein are aqueous acidic media, e.g., water and aqueous solutions of one or more organic and/or inorganic compounds such as alcohols, aldehydes, ketones, carboxylic acids, salts of carboxylic acids, esters, ethers, amines, amine oxides, amides, monosaccharides, disaccharides, oligosaccharides, polysaccharides, metal salts of strong and/or weak acids, etc., at a pH of from about 2 to about 6. Since these swelling agents are ordinarily incapable of also acting as suspension agents, once swelling of the bone particles is achieved, it is necessary to combine the swollen particles with a separate biocompatible fluid carrier component which will maintain the particles in substantially uniform distribution throughout the osteogenic composition. Some types of swelling agents, however, can also function as carriers for the swollen bone particles. A particularly advantageous class of swelling agents which also function as carriers for the swollen bone particles are the liquid polyhydroxy compounds and/or the liquid derivatives thereof and liquid solvent solutions of solid or semi-solid polyhydroxy compounds and/or their derivatives. Of course, the polyhydroxy compounds can be used solely as swelling agents in which case some other material must be employed as the carrier or they can be used solely as carriers in which case a different material must be used as the swelling agent.

The expressions "liquid polyhydroxy compound" and "liquid polyhydroxy compound derivative" as employed herein are intended to include those compounds of this type which in the pure or highly concentrated state and at ambient temperature, e.g., 15°–400° C., are flowable liquids. The expressions "solid polyhydroxy compound" and "solid polyhydroxy compound derivative" as employed herein are intended to include those compounds of this type which in the pure or concentrated state and at ambient temperature are normally solid or semi-solid but are soluble in a suitable liquid solvent, e.g., water, physiological saline, ethanol, glycerol, glucose, propylene glycol, polyethylene glycol of from 200–1000 molecular weight, etc., or mixtures thereof. Useful polyhydroxy compounds possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include ethylene glycol, diethylene glycol, triethylene glycol, 1,2-propanediol, glycerol, trimethylolethane, trimethylopropane, erythritol, pentaerythritol, polyalkylene glycols such as the polyethylene glycols, polyvinylalcohols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing, and the like.

Derivatives of the foregoing polyhydroxy compounds, in particular, ester derivatives thereof, are also useful as swelling agents/carriers. For example, liquid and solid monoesters and diesters of glycerol can be used to good effect, the solid esters being dissolved up to the limit of their solubilities in a suitable vehicle, e.g., propylene glycol, glycerol, polyethylene glycol of 200–1000 molecular weight, polyvinylalcohol, etc. Liquid glycerol esters include monacetin and diacetin and solid glycerol esters include such fatty acid monoesters of glycerol as glycerol monolaurate which is preferred, glyceryl monopalmitate, glyceryl monostearate, etc. An especially preferred carrier herein comprises a 10:1 to 1:10 weight mixture of glyceryl monolaurate and glycerol or a 10:1 to 1:10 weight mixture of glycerol and propylene glycol.

In general, aqueous acidic swelling media produce appreciable swelling of demineralized bone particles even with relatively brief periods of contact, e.g., after only 15–30 minutes of contact time. Non-acidic polyhydroxy component swelling agents will generally take considerably longer to provide equivalent results, e.g., 2 to 4 weeks. Accordingly, the adjustment of the pH of a polyhydroxy compound swelling medium to within 2–6 is usually desirable to shorten the requisite swelling time.

The amount of swelling agent used can vary widely provided, of course, that at least an amount sufficient to cause significant swelling of the demineralized bone particles is employed. Suitable weight ratios of preswollen demineralized bone particles to swelling agent are from about 1:20 to about 10:1, preferably from about 1:5 to about 3:1. Where the swelling agent does not function as a carrier for the swollen bone particles (as in the case of the aqueous acidic media), excess swelling agent can, if desired, be separated from the swollen particles, e.g., by filtration, decantation or centrifugation, followed by addition of a suitable carrier such as any of the polyhydroxy compounds mentioned above. Contact times can also vary widely depending on the nature of the swelling agent selected as previously noted. Thus, e.g., suitable contact times can range from about 30 minutes to 100 hours or more with acidified media generally providing faster results.

The amount of swollen demineralized bone particles which can be incorporated into the flowable osteogenic composition of this invention can vary widely with amounts of from about 5 to about 90 weight percent, and preferably from about 20 to about 80 weight percent, being entirely suitable in most cases, the balance of the composition being made up largely of the carrier component.

One or more substances which modify the physical characteristics of the osteogenic composition of this invention can be added thereto. Thus, e.g., any of various thixotropic, suspension and/or thickening agents can be added to the composition to affect its rheological or flow characteristics in some desirable way. For a variety of applications of the flowable osteogenic composition herein, it may be desirable to formulate the composition as a shape-sustaining moldable mass, e.g., of putty-like consistency, employing a thickening agent such as a solution of polyvinyl alcohol, polyvinylpyrrolidone, cellulosic ester such as hydroxypropyl methylcellulose, carboxyl methylcellulose, pectin, food-grade texturizing agent, gelatin, dextran, collagen, starch, hydrolyzed polyacrylonitrile, hydrolyzed polyacrylamide, polyelectrolyte such as polyacrylic acid salt, etc.

Any variety of medically/surgically useful substances can be incorporated in the flowable osteogenic composition of this invention, e.g., by adding the substance(s) to the swollen demineralized bone particle component, by soaking or immersing the swollen demineralized bone particles in a solution or dispersion of the desired substance(s), by adding the substance(s) to the carrier component of the composition or by adding the substance(s) directly to the flowable osteogenic composition. Medically/surgically useful substances which can be readily incorporated in the osteogenic composition of this invention include, e.g., collagen and insoluble collagen derivatives, hydroxy apatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamicin, etc.; amino acids, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and, nucleic acids. The amounts of such optionally added substances can vary widely with optimum levels being readily determined in a specific case by routine experimentation.

To facilitate on-site preparation of the osteogenic composition herein, the swollen demineralized bone particles and carrier (the latter containing any of the optional ingredients identified above) can be stored in separate packages or containers under sterile conditions and brought together in intimate admixture at the moment of use for immediate application to a bone defect site employing any suitable means, e.g., a syringe, spatula, etc. U.S. Pat. No. 4,458,733, the contents of which are incorporated by reference herein, describes a combined storage mixing and application device which can be adapted to perform the foregoing functions of storage, mixing and application. Alternatively, the osteogenic composition can be prepared well in advance and stored under sterile conditions until required for use, e.g., in the barrel of a syringe or other suitable applicator device.

The osteogenic composition of this invention can be applied to a bone defect site in a variety of ways, e.g., by packing the site with the composition provided in the form of a highly viscous paste or shape-retaining moldable mass. Among the bone repair applications for which the use of the osteogenic composition of this invention is eminently suited are: standard or custom arthroplasty prosthesis; reconstruction of skeletal or other osseous defects; enhancing or augmenting the effectiveness of internal and external fixation devices, bone plates, etc.; as a replacement of corticocancellous strips, and so forth.

The following examples are illustrative of the preparation of the flowable osteogenic composition of this invention.

EXAMPLE 1

A. Preparation of Demineralized Bone Particles

A quantity of human allogenic cortical bone which has been pulverized and sieved to an average particle size of from about 100 to about 300 microns (greatest dimension) is introduced into a reactor which is then sealed. A 70 weight percent ethanol solution at a rate of 30 milliliters per gram of bone particles is introduced into the reactor followed by agitation for 1 hour (Bolander et al., *Journal of Bone and Joint Surgery*, Vol. 68-A, No. 8 (Oct. 1986)) to effect defatting and disinfecting of the particles. Following drainage of the ethanol, a 0.6N solution of HCl at 50 ml per gram of bone is introduced into the reactor (Bolander et al., ibid.), the reaction proceeding for 3 hours (Glowackie, *AATB Workshop*, 11th Annual meeting (1987)). Following drainage of the HCl, the demineralized particles bone are covered and rinsed three times with water for injection (WFI) with the WFI being replaced at 5 minute intervals. Following drainage of the WFI, the demineralized bone particles are completely covered with 0.1M sodium phosphate, a procedure which is repeated until the pH of the solution falls between 6.8 and 7.4.

B. Preparation of Swollen Demineralized Bone Particles

A quantity of demineralized human allogenic cortical bone particles of 100-300 microns average particle size (greatest dimension) obtained by the foregoing procedure are contacted with a large excess of water adjusted to pH 2 and buffered with potassium chloride (0.05 molar). After only 30 minutes of such contact, the particles are observed to exhibited significant swelling, e.g., an average swelling along their greatest dimension of at least about 30 percent. A similar quantity of the bone particles immersed for 30 minutes in water at pH 7.0 and buffered with 0.05 molar potassium phosphate monobasic shows no appreciable swelling demonstrating the critical requirement, in the case of an aqueous swelling agent, that the swelling agent be in the acid pH range.

In addition to becoming swollen, the demineralized bone particles undergo a considerable increase in their transparency, e.g., on the order of about 50%, compared to unswollen bone particles.

C. Preparation of Flowable Osteogenic Composition

Following removal of excess aqueous swelling agent, the swollen demineralized bone particles, 25 gm, and injectable grade glycerol, 95 gm, are thoroughly mixed to provide a flowable osteogenic composition of paste-like consistency. The composition is readily applied to a bone defect site, e.g., employing a syringe, spatula, dental gun or other suitable device.

EXAMPLE 2

The demineralized bone particles of Example 1 are combined with a flowable mixture of 50 weight percent fructose and 50 weight percent dextrose at three different levels to provide flowable osteogenic compositions of paste-like consistency containing 25, 35 and 50 weight percent demineralized bone particles. The osteogenic composition remains firm, smooth and of even composition throughout and hardens in air over a period of 8-12 hours.

Similar results are obtained employing an aqueous sucrose solution as the liquid polyhydroxy compound carrier for the swollen demineralized bone particles.

EXAMPLE 3

A quantity of demineralized human allogenic bone particles of 100-300 microns average particle size (greatest dimension), 25 gm, is thoroughly mixed with injectable grade glycerol, 95 gm, at neutral pH. After 24 hours, no appreciable swelling of the demineralized bone particles is observed. However, after about 3-4 weeks, the demineralized bone particles will have undergone significant swelling, e.g., at least about 30 percent relative to the pre-swollen particles. The resulting osteogenic composition exhibits a paste-like consistency.

EXAMPLES 4-5

Moldable, shape-sustaining osteogenic compositions in accordance with the invention are prepared by uniformly mixing the swollen demineralized bone particles of Example 1 with dextran (clinical grade, molecular weight of from 60,000-90,000). The formulations of two such compositions are as follows (all percentages by weight):

|  | Example 4 | Example 5 |
|---|---|---|
| Swollen Demineralized Bone Particles of Example 1 | 50% | 10% |
| Dextran | 10% | 45% |
| Water | 40% | 45% |

What is claimed is:

1. A flowable osteogenic composition which comprises from about 5 to about 90 weight percent swollen demineralized autogenous or allogenic bone particles exhibiting an average increase in volume and/or weight of at least about 10 percent following contact of the unswollen demineralized bone particles with a demineralized bone particle swelling agent and from about 10 to about 95 weight percent of a biocompatible fluid carrier selected from a member of the group consisting of liquid polyhydroxy compound, liquid ester of a polyhydroxy compound, liquid solution of a solid polyhydroxy compound, liquid solution of a solid ester of a polyhydroxy compound and mixtures thereof, wherein the polyhydroxy compound is selected from the group consisting of acyclic polyhydric alcohols, polyalkylene glycols, non-reducing sugars, sugar alcohols, sugar acids, monosaccharides, disaccharides, water-soluble or water dispersible oligosaccharides, polysaccharides and mixtures thereof.

2. The composition of claim 1 containing at least one additional component selected from the group consisting of antiviral agent, antimicrobial agent, antibiotic agent, amino acid, peptide, vitamin, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxy apatite and penetraction enhancer.

3. The swollen demineralized bone particles of claim 1 exhibiting an average increase in volume and/or weight of at least about 20 percent following contact of the unswollen demineralized bone particles with the demineralized bone particle swelling agent.

4. The swollen demineralized bone particles of claim 1 exhibiting an average increase in volume and/or weight of at least about 30 percent following contact of the unswollen demineralized bone particles with the demineralized bone particle swelling agent.

5. The composition of claim 1 wherein the swollen demineralized bone particles have an average maximum dimension of from about 0.01 to about 10 mm.

6. The composition of claim 1 wherein the carrier is glyceryl monolaurate dissolved in a solvent selected from the group consisting of propylene glycol, glycerol, monoacetin, diacetin, liquid polyethylene glycol and mixtures thereof.

7. The composition of claim 1 containing from about 20 to about 80 weight percent swollen demineralized bone particles and from about 20 to about 80 weight percent carrier.

8. The composition of claim 1 wherein the carrier is selected from the group consisting of glycerol, glycerol monoester and glycerol diester.

9. The composition of claim 1 wherein the carrier is selected from the group consisting of monosaccharide, monosaccharide ester, disaccharide, disaccharide ester, oligosaccharide, oligosaccharide ester and mixtures thereof.

10. The composition of claim 10 wherein the carrier is dextran.

11. A flowable osteogenic composition which comprises from about 5 to about 90 weight percent swollen demineralized autogenous or allogenic bone particles exhibiting an average increase in volume and/or weight of at least about 10 percent following contact of the unswollen demineralized bone particles with a demineralized bone particle swelling agent and from about 10 to about 95 weight percent of a biocompatible fluid carrier selected from a member of the group consisting of liquid polyhydroxy compound, liquid ester of a polyhydroxy compound, liquid solution of a solid polyhydroxy compound, liquid solution of a solid ester of a polyhydroxy compound and mixtures thereof, wherein the polyhydroxy compound is selected from the group consisting of ethylene glycol, diethylene glycol, triethylene glycol, 1,2-propanediol, glycerol, trimethylolethane, trimethylopropane, erythritol, pentaerythritol, polyethylene glycols, polyvinylalcohols, xylitol, sorbitol, mannitol, dulcitol, arabinose, xylose, ribose, adonitol, arabitol, rhamose, inositol, fructose, galactose, glucose, mannose, sorbose, sucrose, dextrose, maltose, lactose, maltitol, lactitol, stachyose, maltopentaose, eyclomaltohexaose, carrageenan, agar, dextran, alginic acid, guar gum, gum tragacanth, locust bean gum, gum arabic, xanthan gum, amylose and mixtures thereof.

12. The composition of claim 1 wherein the carrier is a liquid solution of sucrose.

13. The composition of claim 1 wherein the carrier is an aqueous solution of sucrose.

14. The composition of claim 1 wherein the carrier is a liquid solution of a fatty acid monoester of glycerol.

15. The composition of claim 1 wherein the carrier is a fatty acid monoester dissolved in a solvent which is a different liquid polyhydroxy compound and/or ester thereof.

16. A flowable osteogenic composition which comprises from about 5 to about 90 weight percent swollen demineralized autogenous or allogenic bone particles exhibiting an average increase in volume and/or weight of at least about 10 percent following contact of the unswollen demineralized bone particles with a demineralized bone particle swelling agent and from about 10 to about 95 weight percent of a biocompatible fluid carrier selected from a member of the group consisting of liquid polyhydroxy compound, liquid ester of a polyhydroxy compound, liquid solution of a solid polyhydroxy compound, liquid solution of a solid ester of a polyhydroxy compound and mixtures thereof, wherein the carrier is a fatty acid monoester dissolved in a solvent selected from the group consisting of propylene glycol, glycerol, monoacetin, diacetin, liquid polyethylene glycol and mixtures thereof.

17. The composition of claim 1 wherein the carrier is glycerol monolaurate dissolved in a solvent.

18. The composition of claim 1 wherein the carrier is glycerol monolaurate dissolved in a solvent which is a different liquid polyhydroxy compound and/or ester thereof.

* * * * *